United States Patent
Lee et al.

(10) Patent No.: US 11,066,418 B2
(45) Date of Patent: Jul. 20, 2021

(54) COMPOUND AND THIN FILM TRANSISTOR AND ELECTRONIC DEVICE

(71) Applicant: Samsung Electronics Co., Ltd., Suwon-si (KR)

(72) Inventors: Don-Wook Lee, Seoul (KR); Jeong Il Park, Seongnam-si (KR); Eun Kyung Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/693,715

(22) Filed: Nov. 25, 2019

(65) Prior Publication Data

US 2020/0165268 A1    May 28, 2020

(30) Foreign Application Priority Data

Nov. 26, 2018 (KR) .......... 10-2018-0147720
Nov. 14, 2019 (KR) .......... 10-2019-0145888

(51) Int. Cl.
| | | |
|---|---|---|
| C07D 517/04 | (2006.01) | |
| H01L 51/05 | (2006.01) | |
| H01L 51/00 | (2006.01) | |
| C07D 495/04 | (2006.01) | |
| C07D 517/22 | (2006.01) | |

(52) U.S. Cl.
CPC .......... *C07D 517/04* (2013.01); *C07D 495/04* (2013.01); *C07D 517/22* (2013.01); *H01L 51/0071* (2013.01); *H01L 51/0558* (2013.01)

(58) Field of Classification Search
CPC .................. C07D 517/22; H01L 51/0071
See application file for complete search history.

(56) References Cited

U.S. PATENT DOCUMENTS

| | | |
|---|---|---|
| 7,816,673 B2 | 10/2010 | Park et al. |
| 8,124,964 B2 | 2/2012 | Takimiya et al. |
| 8,138,355 B2 | 3/2012 | Watanabe |
| 8,901,543 B2 | 12/2014 | Adachi et al. |
| 9,318,713 B2 | 4/2016 | Park et al. |

FOREIGN PATENT DOCUMENTS

| | | | |
|---|---|---|---|
| JP | 2006290192 A | | 10/2006 |
| JP | 2007067262 | * | 3/2007 |
| JP | 4581062 B2 | | 11/2010 |
| JP | 5167560 B2 | | 3/2013 |
| JP | 2013191821 A | | 9/2013 |
| JP | 5716781 B2 | | 5/2015 |
| JP | 2016050207 A | | 4/2016 |
| JP | 2017210449 A | | 11/2017 |
| KR | 20150056051 A | | 5/2015 |
| WO | WO-20090009790 A1 | | 1/2009 |

OTHER PUBLICATIONS

Machine translation of JP 2007067262 (Year: 2007).*
STN search where n1 is zero, Nov. 28, 2020 (Year: 2020).*
Park et al. "Dibenzothiopheno[6,5-b:6',5'-f]thieno[3,2-b]thiophene (DBTTT): High-Performance Small-Molecule Organic Semiconductor for Field-Effect Transistors" J. Am. Chem. Soc. 2015, 137, 12175-12178.

* cited by examiner

*Primary Examiner* — Noble E Jarrell
(74) *Attorney, Agent, or Firm* — Harness, Dickey & Pierce, P.L.C.

(57) ABSTRACT

Disclosed are a compound represented by Chemical Formula 1A or 1B, an organic thin film, a thin film transistor, and an electronic device.

[Chemical Formula 1A]

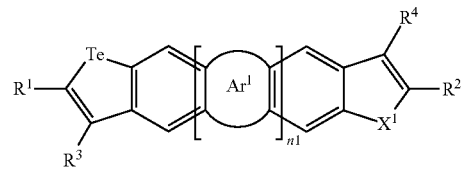

[Chemical Formula 1B]

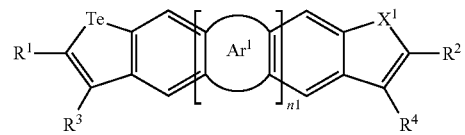

In Chemical Formulae 1A and 1B, $X^1$, $Ar^1$, $R^1$ to $R^4$, and $n_1$ are the same as described in the detailed description.

17 Claims, 1 Drawing Sheet

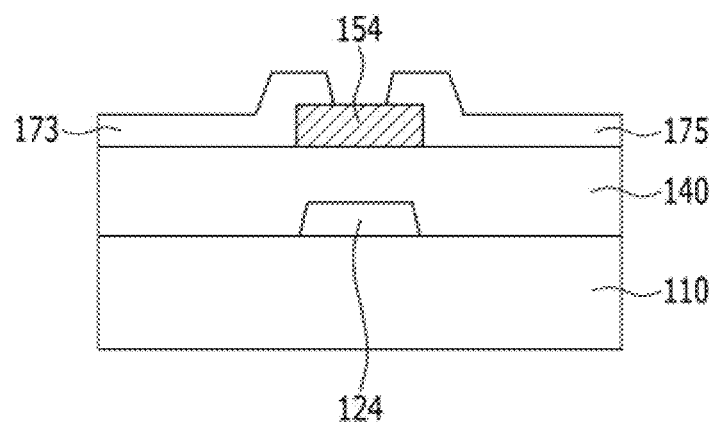

COMPOUND AND THIN FILM TRANSISTOR AND ELECTRONIC DEVICE

CROSS-REFERENCE TO RELATED APPLICATION

This application claims priority to and the benefit of Korean Patent Application No. 10-2018-0147720 filed in the Korean Intellectual Property Office on Nov. 26, 2018, and Korean Patent Application No. 10-2019-0145888 filed in the Korean Intellectual Property Office on Nov. 14, 2019, the entire contents of each of which is incorporated herein by reference.

BACKGROUND

1. Field

Example embodiments of a compound, a thin film transistor, and an electronic device are described below.

2. Description of the Related Art

Electronic devices like such as liquid crystal displays (LCD) or organic light emitting diode (OLED) displays include thin film transistors (TFT) as three-terminal elements. The TFTs are often used as switches or driving devices in electronic devices.

Organic thin film semiconductor may be made into a fiber or a film due to the characteristics of organic materials, and thus organic semiconductor materials are drawing attention as core elements for flexible display devices. The organic thin film transistor may be manufactured using a solution process such as inkjet printing, and may be easily applied to a large area flat panel display where more energetic deposition processes, like CVD or PCD, may have limits.

Research on using organic semiconductor for organic thin film transistor (OTFT), instead of inorganic semiconductors such as a silicon (Si), is being actively conducted.

SUMMARY

An example embodiment provides a compound applicable to an electronic device such as a thin film transistor. Another embodiment provides an organic thin film including the compound. Yet another embodiment provides a thin film transistor including the compound. Still another embodiment provides an electronic device including the thin film transistor.

According to an embodiment, a compound represented by Chemical Formula 1A or 1B is provided.

[Chemical Formula 1A]

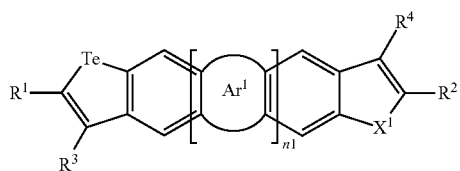

[Chemical Formula 1B]

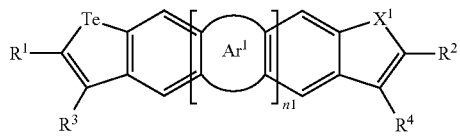

In Chemical Formulae 1A and 1B $X^1$ is O, S, Se, or Te. $Ar^1$ represents an aromatic ring and n1 represents either 0 or 1. For example, $Ar^1$ may be at least one substituted or unsubstituted benzene, at least one substituted or unsubstituted furan, at least one substituted or unsubstituted thiophene, at least one substituted or unsubstituted selenophene, at least one substituted or unsubstituted tellurophene, or a fused ring of the foregoing two or more. $R^1$ to $R^4$ are each independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

$Ar^1$ may be one of the substituted or unsubstituted rings listed in Group 1.

[Group 1]

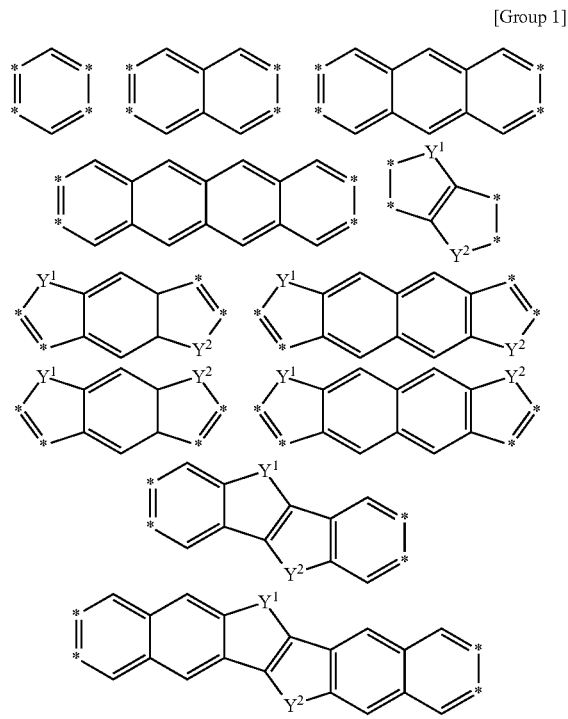

In Group 1, $Y^1$ and $Y^2$ are each independently one of O, S, Se, and Te, and the symbol "*" is a linking point with Chemical Formula 1A or 1B.

$Ar^1$ may be one of substituted or unsubstituted rings listed in Group 1-1 and $X^1$ of Chemical Formula 1A or 1B may be different from $Y^1$ and $Y^2$ of Group 1-1.

[Group 1-1]

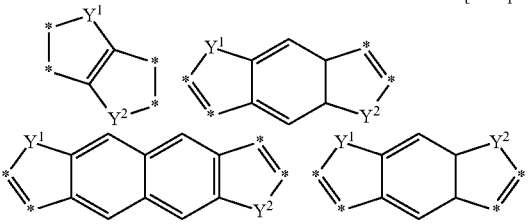

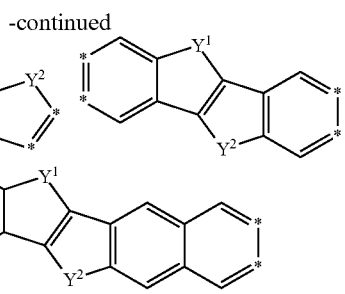

In Group 1-1, $Y^1$ and $Y^2$ are each independently one of O, S, Se, and Te, and * is a linking point with Chemical Formula 1A or 1B.

$X^1$ may be Se or Te and $Y^1$ and $Y^2$ may each independently be S. $R^1$ and $R^2$ may be different from each other.

One of $R^1$ and $R^2$ may be hydrogen and the other of $R^1$ and $R^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

One of $R^1$ and $R^2$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of $R^1$ and $R^2$ may be a substituted or unsubstituted C3 to C30 branched alkyl group, a substituted or unsubstituted C4 to C30 branched alkenyl group, a substituted or unsubstituted C4 to C30 branched alkynyl group, or a combination thereof.

One of $R^1$ and $R^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^1$ and $R^2$ may be a substituted or unsubstituted C6 to C30 aryl group, a substituted or unsubstituted C6 to C30 aryloxy group, a substituted or unsubstituted C3 to C30 heteroaryl group, or a combination thereof.

According to another embodiment, an organic thin film including the compound is provided.

According to another embodiment, a thin film transistor includes a gate electrode, an organic semiconductor overlapping with the gate electrode, and a source electrode and a drain electrode electrically connected to the organic semiconductor, wherein the organic semiconductor includes a compound represented by Chemical Formula 1 A or 1B.

According to another embodiment, an electronic device including the organic thin film or the thin film transistor is provided.

The compound may be effectively applied with deposition or solution processes. The compound may exhibit improved crystallinity and improved charge mobility.

BRIEF DESCRIPTION OF THE DRAWINGS

FIG. 1 is a cross-sectional view showing a thin film transistor according to an embodiment.

DETAILED DESCRIPTION

Example embodiments will hereinafter be described in detail, and may be easily performed by a person having an ordinary skill in the related art. However, this disclosure may be embodied in many different forms and is not to be construed as limited to the example embodiments set forth herein.

In the drawing, the thicknesses of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when a definition is not otherwise provided, "thin film" is a film or a layer having a thickness of 1Å to 1000 μm.

As used herein, when a definition is not otherwise provided, "substituted" refers to the replacement of a hydrogen of a compound or a group by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" refers to the inclusion of one to four heteroatoms selected from N, O, S, Se, Te, Si, and P.

As used herein, when a definition is not otherwise provided, "alkyl group" refers to a linear or branched, saturated, monovalent hydrocarbon group (e.g., a methyl group, an ethyl group, a propyl group, an isobutyl group, a sec-butyl group, a tert-butyl group, a pentyl group, an iso-amyl group, a hexyl group, etc.).

As used herein, when a definition is not otherwise provided, "alkenyl group" refers to a linear or branched, saturated, monovalent hydrocarbon group (e.g., an ethenyl group) having at least one carbon-carbon double bond.

As used herein, when a definition is not otherwise provided, "alkynyl group" refers to a linear or branched saturated monovalent hydrocarbon group including at least one carbon-carbon triple bond (e.g., an ethynyl group).

As used herein, when a definition is not otherwise provided, "alkoxy group" refers to an alkyl group that is linked via oxygen, for example a methoxy, an ethoxy, and a sec-butyloxy group.

As used herein, when a definition is not otherwise provided, "aryl group" refers to a monovalent functional group formed by the removal of one hydrogen atom from one or more rings of an arene, e.g., phenyl or naphthyl. Arene refers to a hydrocarbon having an aromatic ring, and includes monocyclic and polycyclic hydrocarbons, wherein the additional ring(s) of the polycyclic hydrocarbon may be aromatic or nonaromatic.

As used herein, when a definition is not otherwise provided, "heteroaryl group" may refer to a monovalent functional group formed by the removal of one hydrogen atom from one or more rings of a heteroarene.

As used herein, when a definition is not otherwise provided, "arylalkyl group" refers to an alkyl group in which at least one hydrogen atom is replaced by an aryl group.

As used herein, when a definition is not otherwise provided, "alkylaryl group" refers to an aryl group in which at least one hydrogen atom is replaced by an alkyl group.

As used herein, when a definition is not otherwise provided, "aryloxy group" refers to an aryl group that is linked via oxygen, and the aryl group is the same as described above.

As used herein, when a definition is not otherwise provided, "arylalkyl group" refers to an aryl group in which a part of the hydrogen atoms is replaced by a lower alkylene, for example methylene, ethylene, propylene, and the like. For example, it may be a benzyl group, a phenylethyl group, and the like.

As used herein, when a definition is not otherwise provided, "cycloalkyl group" refers to a monovalent functional group having one or more saturated rings in which all ring members are carbon, e.g., a cyclopentyl group and a cyclohexyl group.

As used herein, when a definition is not otherwise provided, "heteroalkyl group" refers to the alkyl group defined above in which methylene ($-CH_2-$) is replaced by $-O-$, $-S-$, $-S(=O)_2-$, $-Se-$, or $-NR-$ (wherein R is each independently hydrogen or a C1 to C10 alkyl group).

As used herein, when a definition is not otherwise provided, "arylheteroalkyl group" refers to the heteroalkyl group defined above in which at least an aryl group replaces one of the hydrogen atoms.

As used herein, when a definition is not otherwise provided, "heteroarylalkyl group" refers to the alkyl group defined above in which at least a heteroaryl group replaces one of the hydrogen atoms.

As used herein, when a definition is not otherwise provided, "alkylheteroaryl group" refers to the heteroaryl group defined above in which at least an alkyl group replaces one of the hydrogen atoms.

As used herein, when a definition is not otherwise provided, "aromatic ring" refers to a functional group in which all atoms in the cyclic functional group have a p-orbital, and wherein these p-orbitals are conjugated. For example, the aromatic ring may be a C6 to C20 aryl group.

Hereinafter, a compound according to an example embodiment is described.

A compound according to an embodiment is represented by Chemical Formula 1A or 1B.

[Chemical Formula 1A]

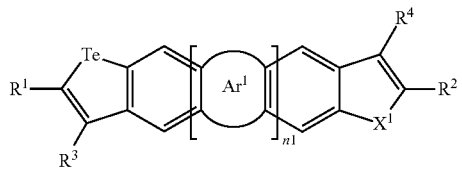

[Chemical Formula 1B]

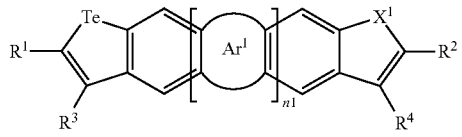

In Chemical Formulae 1A and 1B $X^1$ may represent O, S, Se, or Te.

$Ar^1$ may represent an aromatic structure containing one or more aromatic rings and $n_1$ is either 0 or 1. For example, $Ar^1$ may be at least one substituted or unsubstituted benzene, at least one substituted or unsubstituted furan, at least one substituted or unsubstituted thiophene, at least one substituted or unsubstituted selenophene, at least one substituted or unsubstituted tellurophene, or a fused structure of two or more of the foregoing rings. $R^1$ to $R^4$ may represent an attached functional group, may each be independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

The compound is a fused polycyclic aromatic compound including, as a core structure, a fused polycyclic aromatic ring having a tellurophene at a terminal end. The core structure may have benzo-heterocycles that are fused rings of a pentagonal heterocycle and benzene at both terminal ends, and at least one of the polycyclic aromatic rings may be benzotellurophene. The core structure may be symmetric or asymmetric. The core structure may form a 2-fold symmetric core structure when $X^1$ is for example Te, a rotational order 2 core structure when $X^2$ is for example Te, and may form an asymmetric core structure when $X^2$ is for example O, S, or Se.

The fused polycyclic aromatic compound having a core structure with tellurophene at the terminal end may increase overlaps of electron orbitals of the fused polycyclic aromatic compound, and thus improve charge mobility compared to a fused polycyclic aromatic compound with thiophene, selenophene, and/or benzene at the terminal end.

In the case where the core structure may have an asymmetric core structure in which $X^1$ is O, S, or Se, the fused polycyclic aromatic compound may organize into polycrystalline structures with high crystallinity and, thus, further improve charge mobility. In addition, the fused polycyclic aromatic compound having an asymmetric core structure may exhibit liquid crystal property at an tunable temperature range, and thus increase the alignment of molecules. Since the temperature range showing the liquid crystal property may be a relatively low temperature, the process temperature may be further decreased. Accordingly, a semiconductor composed of the fused polycyclic aromatic compound having an asymmetric core structure may have much higher charge mobility due to the high crystallinity and molecular alignment and, simultaneously, have a decrease processing temperature. Accordingly, the semiconductor composed of the fused polycyclic aromatic compound having an asymmetric core may be more resilient to degradation. Thus, a thin film composed of the semiconductor may also be more resilient to damage, like crack formation or stress-strain deformation.

$Ar^1$ may be a substituted or unsubstituted benzene; a substituted or unsubstituted furan; a substituted or unsubstituted thiophene; a substituted or unsubstituted selenophene; a substituted or unsubstituted tellurophene; a substituted or unsubstituted naphthalene; a substituted or unsubstituted anthracene; a substituted or unsubstituted tetracene; or a fused combination of one or more of these rings. For example, $Ar^1$ may be a fused ring of at least one substituted or unsubstituted benzene and at least one substituted or unsubstituted furan; a fused ring of at least one substituted or unsubstituted benzene and at least one substituted or unsubstituted thiophene; a fused ring of at least one substituted or unsubstituted benzene and at least one substituted or unsubstituted selenophene; a fused ring of at least one substituted or unsubstituted benzene and at least one substituted or unsubstituted tellurophene; a fused ring of at least two substituted or unsubstituted furan; a fused ring of at least two substituted or unsubstituted thiophene; a fused ring of at least two substituted or unsubstituted selenophene; a fused ring of at least two substituted or unsubstituted tellurophene; a fused ring of at least one substituted or unsubstituted furan and at least one substituted or unsubstituted thiophene; a fused ring of at least one substituted or unsubstituted furan and at least one substituted or unsubstituted selenophene; a fused ring of at least one substituted or unsubstituted furan and at least one substituted or unsubstituted tellurophene; a fused ring of at least one substituted or unsubstituted thiophene and at least one substituted or unsubstituted selenophene; a fused ring of at least one substituted or unsubstituted thiophene and at least one substituted or unsubstituted tellurophene; or a fused ring of at least one substituted or unsubstituted selenophene and at least one substituted or unsubstituted tellurophene, but is not limited thereto.

$Ar^1$ may include one to eight rings, for example one to six rings. For example, $A^1$ may include one of substituted or unsubstituted rings of Group 1.

[Group 1]

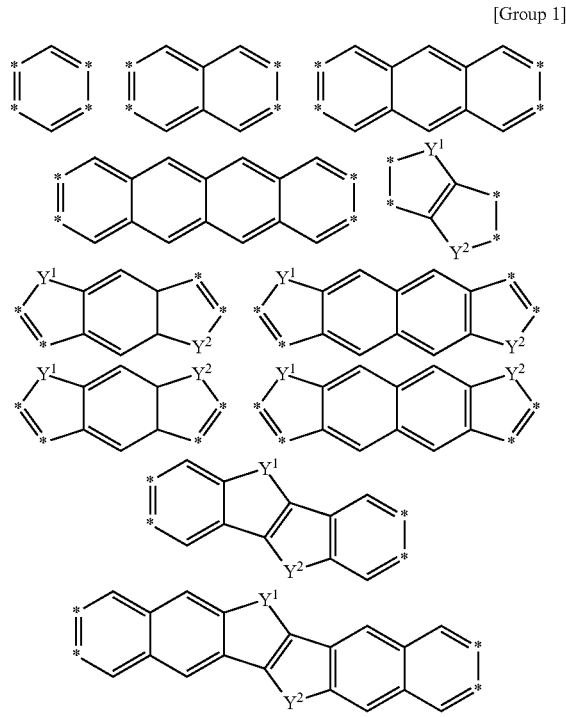

In Group 1, $Y^1$ and $Y^2$ are each independently one of O, S, Se, and Te, and the "*" represents a linking point with Chemical Formula 1A or 1B.

In the rings listed in Group 1, $Y^1$ and $Y^2$ may be the same, may be each independently S, may be each independently Se, may be each independently Te, or may be different from each other. For example, in the rings listed in Group 1, one of $Y^1$ and $Y^2$ may be S and the other of $Y^1$ and $Y^2$ may be Se or Te; or one of $Y^1$ and $Y^2$ may be Se and the other of $Y^1$ and $Y^2$ may be Te.

$Ar^1$ may be one of substituted or unsubstituted rings listed in Group 1-1.

[Group 1-1]

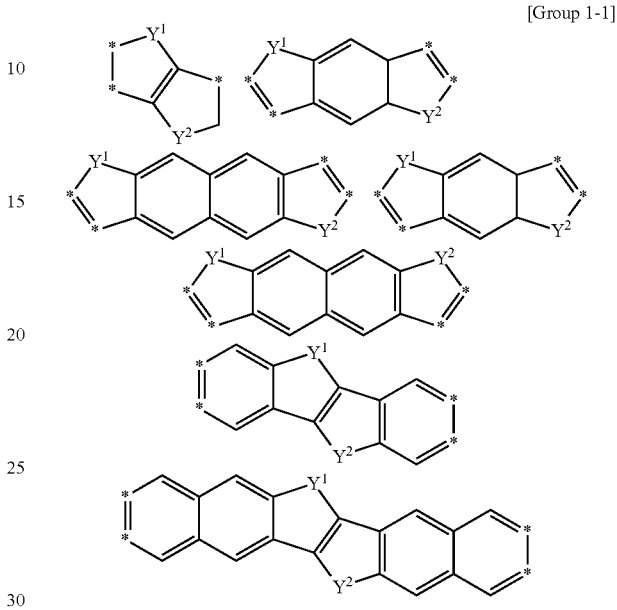

In Group 1-1, $Y^1$ and $Y^2$ are each independently one of O, S, Se, and Te, and "*" is a linking point with Chemical Formula 1A or 1B.

In the rings listed in Group 1-1, $Y^1$ and $Y^2$ may be the same, may be each independently S, may be each independently Se, may be each independently Te, or may be different from each other. For example, in the rings listed in Group 1, one of $Y^1$ and $Y^2$ may be S and the other of $Y^1$ and $Y^2$ may be Se or Te; or one of $Y^1$ and $Y^2$ may be Se and the other of $Y^1$ and $Y^2$ may be Te.

$X^1$ of Chemical Formula 1 A or 1B may be different from each of $Y^1$ and $Y^2$ of Group 1-1. For example, $X^1$ of Chemical Formula 1A or 1B may be Se or Te and $Y^1$ and $Y^2$ of Group 1-1 may be each independently S.

Where $n_1$ is 0, the compound may be a fused polycyclic aromatic compound in which four aromatic rings are fused.

Where $n_1$ is 1, the compound may be a fused polycyclic aromatic compound in which five or more rings are fused. For example, the compound may be a fused polycyclic aromatic compound including as a core structure, a fused polycyclic aromatic ring in which five to twelve rings are fused, for example a fused polycyclic aromatic compound including as a core structure, a polycyclic aromatic ring in which six to ten rings are fused. For example, the compound may be an unsubstituted fused polycyclic aromatic compound.

The fused polycyclic aromatic compound may have at least one substituent and at least one of $R^1$ to $R^4$ may not hydrogen.

For example, the compound may be a fused polycyclic aromatic compound having an asymmetric substituted structure where $R^1$ may be different from $R^2$ and/or $R^3$ may be different from $R^4$.

The compound may have a substituent at one side alone of fused polycyclic aromatic ring. For example, one of $R^1$ and $R^2$ may be hydrogen and the other of $R^1$ and $R^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof. Additionally, one of $R^3$ and $R^4$ may be hydrogen and the other of $R^3$ and $R^4$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

The compound may also have a linear substituent at one side of the fused polycyclic aromatic ring and a nonlinear substituent at the other side of the fused polycyclic aromatic ring.

For example, one of $R^1$ and $R^2$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of $R^1$ and $R^2$ may be a substituted or unsubstituted C3 to C30 branched alkyl group, a substituted or unsubstituted C4 to C30 branched alkenyl group, a substituted or unsubstituted C4 to C30 branched alkynyl group, or a combination thereof.

Additionally, one of $R^3$ and $R^4$ may be a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof and the other of $R^3$ and $R^4$ may be a substituted or unsubstituted C3 to C30 branched alkyl group, a substituted or unsubstituted C4 to C30 branched alkenyl group, a substituted or unsubstituted C4 to C30 branched alkynyl group, or a combination thereof.

The compound may have a noncyclic substituent at one side of the fused polycyclic aromatic ring and a cyclic substituent at the other side of the fused polycyclic aromatic ring. For example, one of $R^1$ and $R^2$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^1$ and $R^2$ may be a substituted or unsubstituted C6 to C30 aryl group, a substituted or unsubstituted C6 to C30 aryloxy group, a substituted or unsubstituted C3 to C30 heteroaryl group, or a combination thereof. Additionally, one of $R^3$ and $R^4$ may be a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof and the other of $R^3$ and $R^4$ may be a substituted or unsubstituted C6 to C30 aryl group, a substituted or unsubstituted C6 to C30 aryloxy group, a substituted or unsubstituted C3 to C30 heteroaryl group, or a combination thereof.

The compound may have a cyclic substituent at one side of the fused polycyclic aromatic ring and a heterocyclic substituent at the other side of the fused polycyclic aromatic ring. For example, one of $R^1$ and $R^2$ may be a substituted or unsubstituted C6 to C30 aryl group or a substituted or unsubstituted C6 to C30 aryloxy group and the other of $R^1$ and $R^2$ may be a substituted or unsubstituted C3 to C30 heteroaryl group. Additionally, one of $R^3$ and $R^4$ may be a substituted or unsubstituted C6 to C30 aryl group or a substituted or unsubstituted C6 to C30 aryloxy group and the other of $R^3$ and $R^4$ may be a substituted or unsubstituted C3 to C30 heteroaryl group.

For example, one of $R^1$ and $R^2$ may include a substituted or unsubstituted C6 to C30 aryl group or a substituted or unsubstituted C3 to C30 heteroaryl group, and one of $R^1$ and $R^2$ may include a group represented by one of Chemical Formulae 2A to 2C.

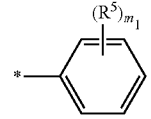

[Chemical Formula 2A]

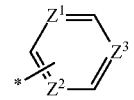

[Chemical Formula 2B]

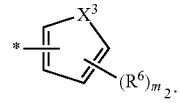

[Chemical Formula 2C]

In Chemical Formulae 2A to 2C $Z^1$ to $Z^3$ may each be N or $CR^a$; one of $Z^1$ to $Z^3$ may be N. $X^3$ is O, S, Se, Te, $NR^b$, or $CR^cR^d$; $m_1$ is an integer of 0 to 5, $m_2$ is an integer of 0 to 3; and $R^5$, $R^6$ and $R^a$ to $R^d$ are each independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof.

When $m_1$ is 2 or more, each $R^5$ is the same or different and adjacent $R^5$'s are each independently present and are bound to form a ring, and when $m_2$ is 2 or more, each $R^6$ is the same or different and adjacent $R^5$'s are each independently present and are bound to form a ring.

One of $R^3$ and $R^4$ may each independently include hydrogen, a substituted or unsubstituted C6 to C30 aryl group or a substituted or unsubstituted C3 to C30 heteroaryl group, and a group represented by one of Chemical Formulae 2A to 2C.

The compound may be for example one of compounds listed in Group 2, but is not limited thereto.

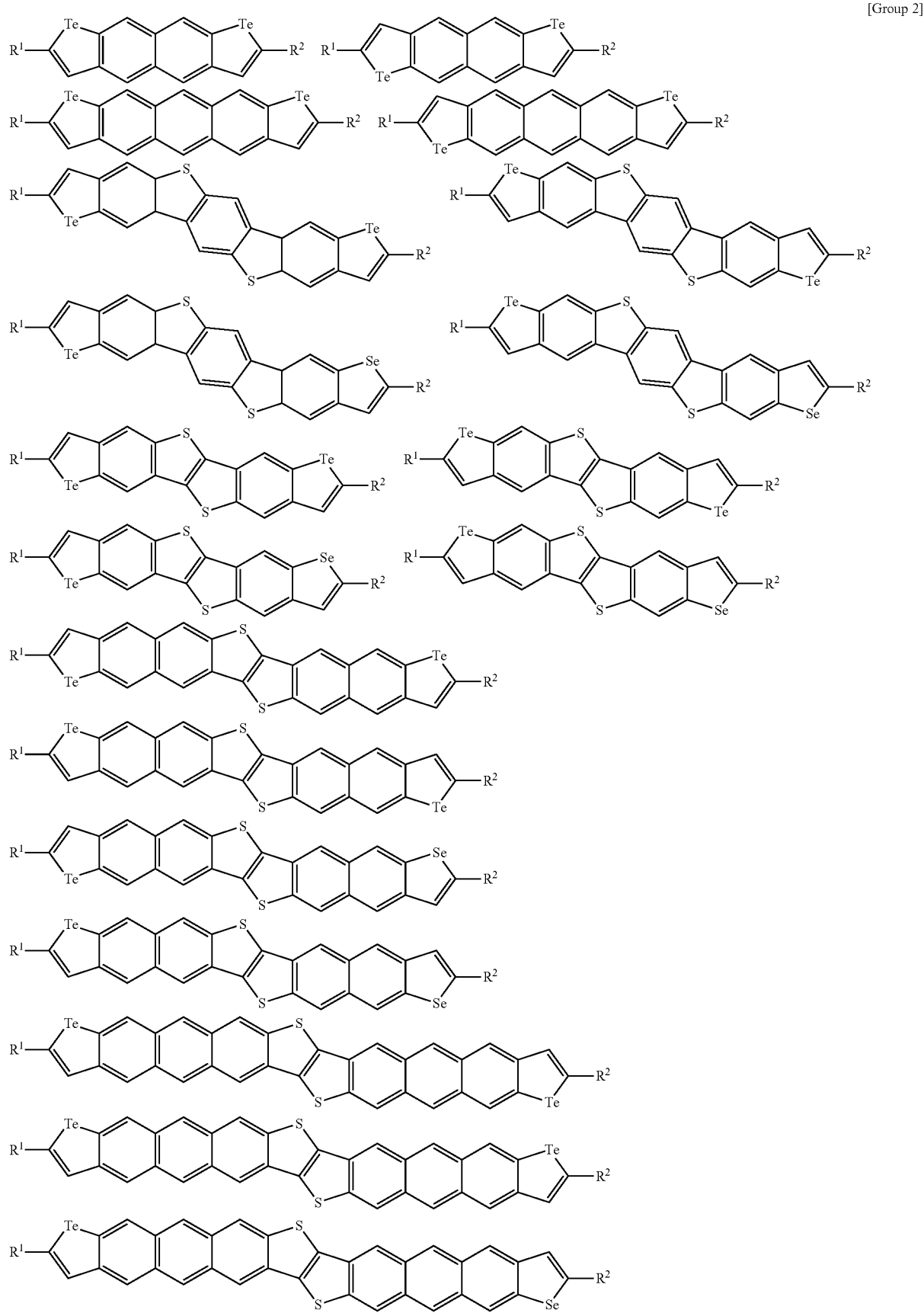

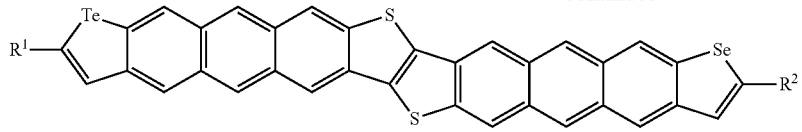

In Group 2, $R^1$ and $R^2$ are the same as described above.

Since tellurophene may have a low reactivity, a new synthesis method may be required for the compound with a tellurophene atom at the terminal end.

A method of synthesizing the compound according to an embodiment includes reacting aldehyde-substituted tellurophene and a cyclic compound substituted with at least two halogens.

For example, a method of synthesizing the compound according to an embodiment may include preparing aldehyde-substituted tellurophene, reacting the aldehyde-substituted tellurophene with a cyclic compound substituted with at least two halogens to obtain a first intermediate, being subjected to formylation of the first intermediate to obtain a second intermediate, and being subjected to a cyclization reaction of the second intermediate to obtain the aforementioned fused polycyclic aromatic compound.

For example, the aldehyde-substituted tellurophene may be tellurophene substituted with aldehyde at the position 2. The first intermediate may be obtained by a nucleophilic addition reaction and a dehydration reaction. The second intermediate may be obtained by supplying t-BuLi and dimethyl formamide to the first intermediate. For example, the second intermediate may be an aldehyde compound.

An acidic catalyst may be supplied in a cyclization reaction. The acidic catalyst may be, for example, Amberlyst 15 (Sigma-Aldrich), but is not limited.

The aforementioned compound may be implemented as an organic thin film. The organic thin film may be a deposition-type thin film formed by a deposition process or a coating-type thin film formed by a solution process.

The organic thin film may be applied to various devices including organic semiconductors. For example, the compound may be applied in a thin film transistor, and may be applied as a charge transport layer and/or an active layer of an electronic device such as a solar cell, an organic light emitting diode (OLED) display, and an organic sensor.

Hereinafter, one example of a thin film transistor including the compound is described with reference to the drawing.

FIG. 1 is a cross-sectional view showing a thin film transistor according to an embodiment.

A gate electrode 124 may be formed on a substrate 110 made of transparent glass, silicon, or plastic. The gate electrode 124 may be connected to a gate line (not shown). The gate line may be used to transfer a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, electrically conductive materials like graphene, CNT and conductive polymers, or a combination thereof.

A gate insulating layer 140 is formed on the gate electrode 124. The gate insulating layer 140 may be made of an organic material and/or an inorganic material. Examples of the organic material may include a soluble compound such as a polyvinyl alcohol-based compound, a polyimide-based compound, a polyacryl-based compound, a polystyrene-based compound, and benzocyclobutene (BCB), and examples of the inorganic material may include a silicon nitride ($SiN_x$) and a silicon oxide ($SiO_2$).

An organic semiconductor 154 may be formed on the gate insulating layer 140. The organic semiconductor 154 may include the aforementioned compound. The organic semiconductor 154 may be formed by a solution process for example spin coating, slit coating, or inkjet printing of a solution including the aforementioned compound. The organic semiconductor 154 may also be formed by vacuum deposition or thermal deposition of the aforementioned compound.

A source electrode 173 and a drain electrode 175 are formed on the organic semiconductor 154. The source electrode 173 and the drain electrode 175 may face each other on the organic semiconductor 154 and face towards the center of the gate electrode 124. The source electrode 173 may be electrically connected to a data line (not shown). The data line may be used to transfer a data signal. The source electrode 173 and the drain electrode 175 may include at least one metal of gold (Au), copper (Cu), nickel (Ni), aluminum (Al), molybdenum (Mo), chromium (Cr), tantalum (Ta), titanium (Ti), an alloy thereof, or a combination thereof or an electrically conductive material like graphene, CNT and conductive polymers.

Although the architecture of the transistor is described as a bottom gate structured thin film transistor, the architecture of the transistor is not limited thereto, and may be other thin film transistor architectures, for example a top gate structured thin film transistor, or to other transistor architectures, for example, metal-oxide-semiconductor field effect transistors, and metal-semiconductor field effect transistors.

The thin film transistor may be applied as a switch or a driving device for various electronic devices. The electronic devices may include, for example, a liquid crystal display (LCD), an organic light emitting diode (OLED) display, an electrophoretic display, an organic photoelectric device, and an organic sensor, but is not limited thereto.

The thin film transistor may be part of an array panel. The thin film transistor array panel may include a plurality of pixels defined by a plurality of gate lines and a plurality of data lines. The plurality of pixels may be arranged in a matrix format along rows and/or columns. Each pixel may include one or more thin film transistors (TFTs) as switching and/or driving elements. The thin film transistors may be regularly arranged along rows and/or columns in the thin film transistor array panel.

The TFT array panel may be part of an electronic device, like an LCD display. A storage capacitor and a liquid-crystal capacitor may be connected as a load to the TFT, with the liquid-crystal capacitor configured to undergo a phase transition when subjected to a sufficient data signal from the data line.

A light source may produce light. The light may be blocked by the liquid-crystal capacitor or may pass through the liquid crystal capacitor and a glass color filter. The glass color filter may have red, green, and/or blue filters.

Though the above describes the TFT array panel as part of an example LCD display, a person having ordinary skill in the art would understand that the array and the thin film transistor could be used as part of other electronic devices such as a light emitting display (LED), an electrophoretic display device, an organic sensor, a wearable device, flexible sensors, mechanical sensors, or other electronic devices.

Hereinafter, the embodiments are illustrated in more detail with reference to illustrative examples. However, a person having ordinary skill would recognize the present scope is not limited thereto.

Synthesis of Compound

Synthesis Example1

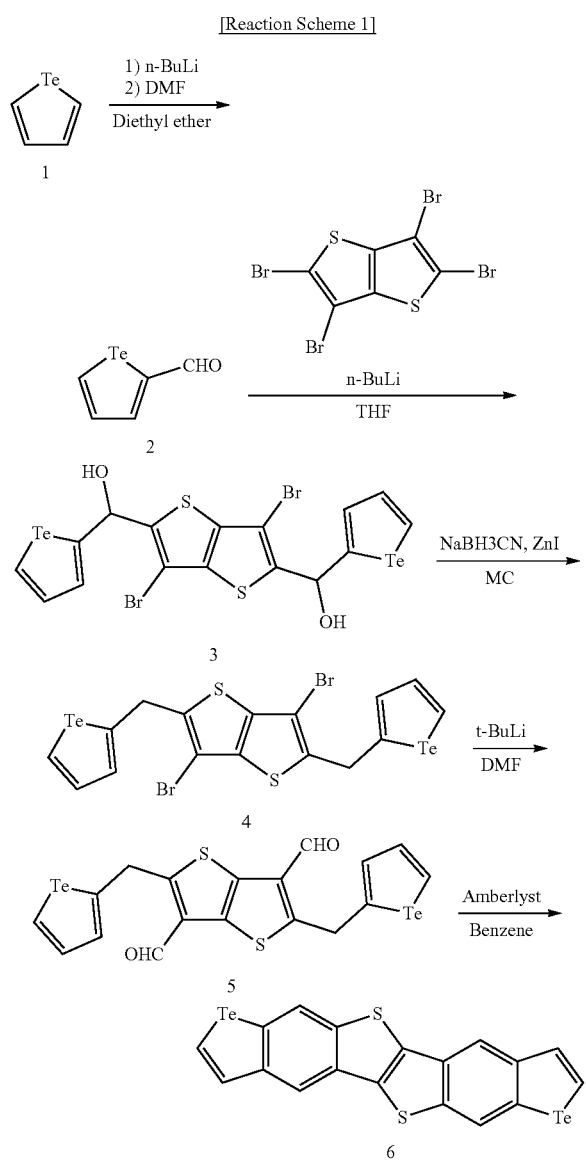

Synthesis of Compound 2

30.0 g (167 mmol) of tellurophene is added to 500 ml of diethylether to prepare a cooled solution (0° C.), n-butyl-lithium (n-BuLi, 2.5 M in hexane, 80 mL, 200 mmol) is added thereto, and the reaction mixture is fervently stirred at room temperature for 30 minutes. Additionally, the reaction mixture is stirred at 50° C. for 4 hours, and when cooled down to −50° C., dimethylformamide is slowly added thereto. Subsequently, the reaction mixture is stirred at room temperature all night long and then diluted with distilled water, and extracted with chloroform. Then, an organic layer is formed from the mixture, dried with magnesium sulfate, and purified through silica column chromatography (ethyl acetate: hexane: chloroform=1:6:1.5 in a volume ratio) to obtain 20.0 g of Compound 2. The yield may be 57.7%.

1H-NMR (300 MHz, CDCl3): δ 9.56 (s, 1H), 9.48 (d, 1H), 8.51 (d, 1H), 8.05 (m, 1H).

Synthesis of Compound 3

13.2 g (28.9 mmol) of tetrabromotheno[3,2-b]thiophene is added to 500 ml of tetrahydrofuran to prepare a cooled solution (−40 ° C.), n-butyllithium (n-BuLi 2.5 M in hexane, 23.1 mL, 57.8 mmol) is added thereto, and when gradually heated up to −5° C., the reaction mixture is fervently stirred for 2 hours. When cooled down to −78° C., Compound 2 is added thereto, and the reaction mixture is stirred at room temperature all night long. Subsequently, ammonium chloride is added to the reaction mixture, and after evaporating a tetrahydrofuran solvent therefrom, ethyl acetate is used for an extraction. Then, an organic layer from the mixture, and is dried with magnesium sulfate to obtain 9.0 g of Compound 3. The yield may be 43.6%.

1H-NMR (300 MHz, CDCl3): δ 8.90 (d, 1H), 7.70 (t, 1H), 7.61 (d, 1H), 6.31 (s, 1H), 2.93 (s, 1H).

Synthesis of Compound 4

9.0 g (12.6 mmol) of Compound 3 is added to 500 ml of dichloromethane to prepare a stirred solution, and 12.9 g (40.4 mmol) of zinc(II) iodide and 11.08 g (176.4 mmol) of sodium cyanoborohydride (NaBH3CN) are slowly added thereto at 0° C. Subsequently, the reaction mixture is stirred for 24 hours, and a saturated ammonium chloride solution is added thereto. The resulting mixture is diluted with dichloromethane and washed several times with water, and the mixture is passed through a silica column and then, dried and evaporated with magnesium sulfate. The dried mixture is purified through silica column chromatography (ethyl acetate: hexane: chloroform=1:6:1.5 in a volume ratio) to obtain 4.2 g of Compound 4. The yield may be 48.9%.

1H-NMR (300 MHz, CDCl3): δ 8.78 (d, 1H), 7.63 (m, 1H), 7.50 (d, 1H), 2.04 (s, 2H).

Synthesis of Compound 5

When 10 ml of tetrahydrofuran is cooled down to −78 ° C., n-BuLi (2.5 M, 1.5 mL, 3.8 mmol) is added thereto, and this solution is added to Compound 4 (1 g, 1.5 mmol) dissolved in 10 mL of the tetrahydrofuran. Subsequently, the obtained mixture is stirred at −78 ° C. for 1 minute, dimethyl formamide (0.46 mL, 6.0 mmol) is added thereto and then, the mixture is stirred at room temperature for 5 minutes. Then, ammonium chloride is added to the reaction mixture, ammonium chloride is added thereto, and then, dimethyl acetate is used for an extraction. Subsequently, an organic layer is formed from the mixture, is dried with magnesium sulfate, and purified through silica column chromatography (CHCl3 100%) to obtain 0.2 g of Compound 5. The yield may be 23%.

1H-NMR (300 MHz, CDCl3): δ 10.19 (s, 1H), 8.81 (d, 1H), 7.64 (m, 1H), 7.52 (d, 1 H), 4.82 (s, 1 H).

Synthesis of Compound 6

2.4 g (10.5 mmol) of Compound 5 is added to 350 ml of dry benzene to prepare a stirred solution, and 15.6 g of Amberlyst is added thereto under a nitrogen atmosphere. Subsequently, the obtained solution is refluxed all night long and then, cooled down to room temperature. Then, floating matters are filtered from the mixture to obtain 0.7 g of Compound 6 in a solid state. The yield may be 31%.

HRMS (m/z): [M]+calcd for C18H8S2Se2 543.816; found 543.928.

Synthesis Example 2

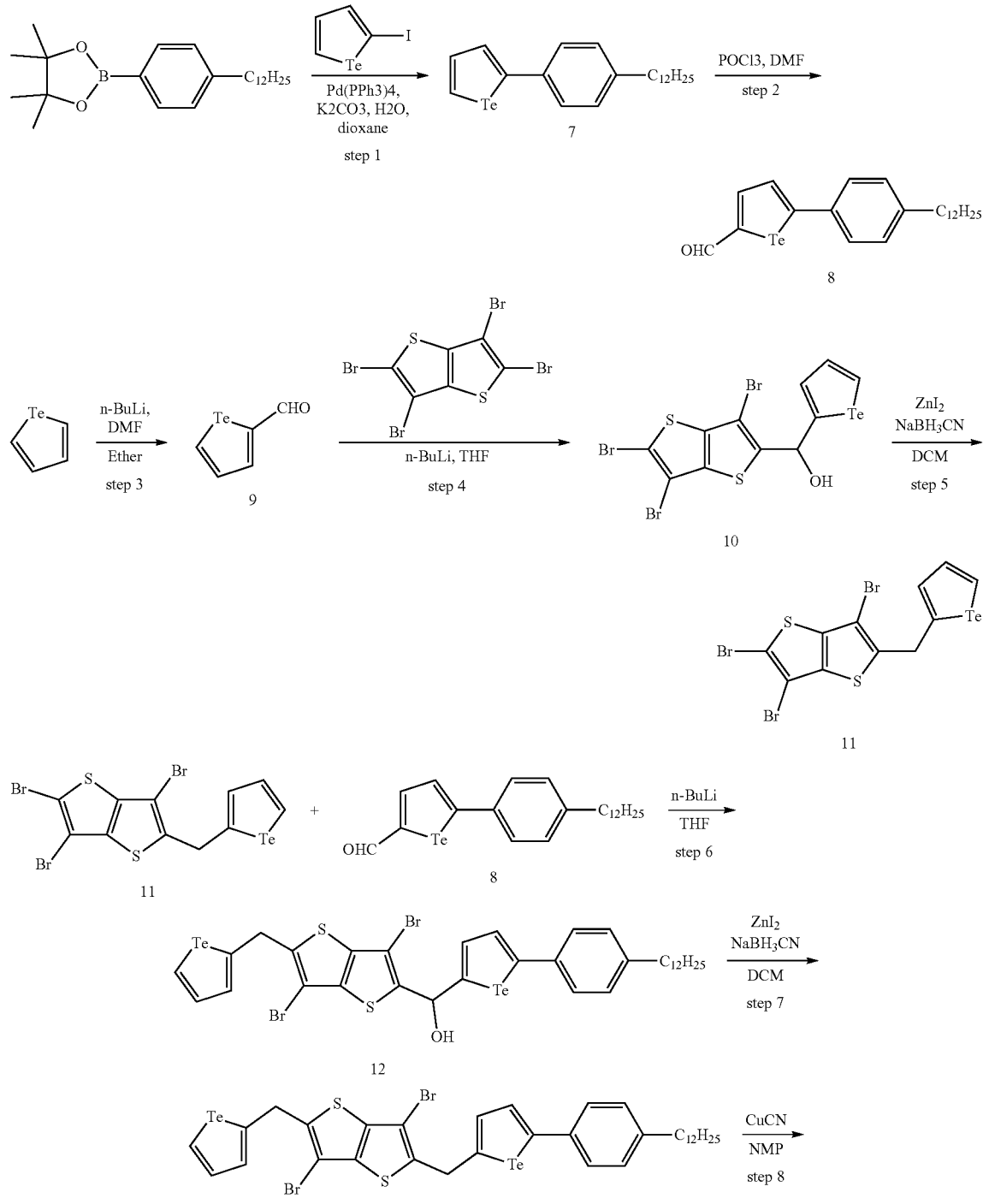

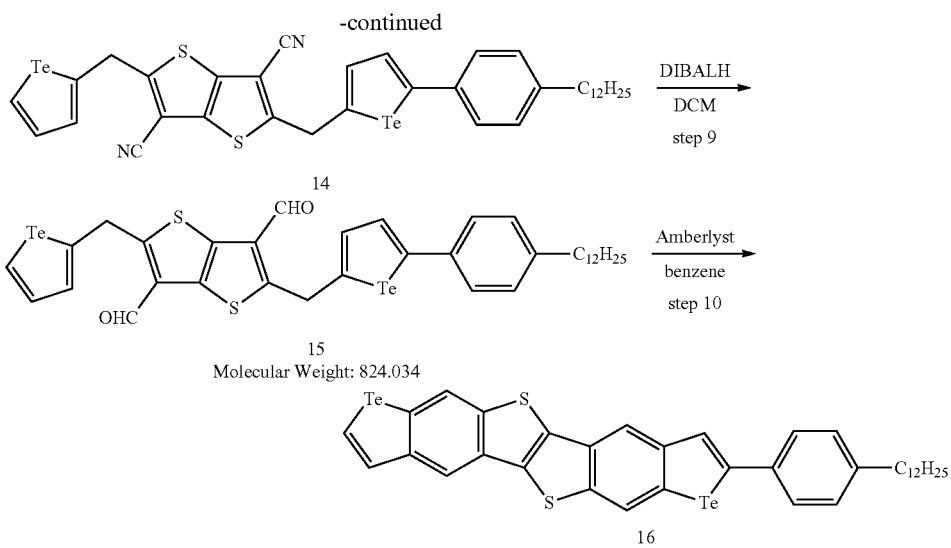

Synthesis of Compound 7

13.6 g (98.2 mmol) of potassium carbonate ($K_2CO_3$) is dissolved in 150 ml of distilled water, 10 g (32.7 mmol) of 2-iodotellurophene dissolved in 450 ml of toluene, 12.2 g (32.7 mmol) of 2-(4-dodecylphenyl)-4,4,5,5-tetramethyl-1,3,2-dioxaborolane, and 5.7 g (4.9 mmol) of palladium (0) ($Pd(PPh_3)_4$) are added thereto and then, refluxed at 140° C. Subsequently, 200 mL of an ammonium chloride saturated solution is added thereto and then, extracted with ethyl acetate and washed several times with water. Then, an organic layer is formed, dried with magnesium sulfate, and purified through silica column chromatography to obtain 18.7 g of Compound 7.
The yield may be 45%.
$^1$H NMR (500 MHz, $CDCl_3$): δ ppm 8.77 (d, 1H), 7.77 (m, 2H), 7.40 (d, 2H), 7.14 (d, 2H), 2.59 (t, 2H), 1.55 (m, 2H), 1.28 (m, 18H), 0.88 (t, 3H).

Synthesis of Compound 8

4.4 ml (47.2 mmol) of phosphorylchloride ($POCl_3$) is slowly added to 9.1 ml (118 mmol) of dimethyl formaldehyde (DMF) at 0° C. and then, stirred for 2 hours. 10 g (23.6 mmol) of Compound 7 is dissolved in 1 L of dichloromethane, and then, the solution is added thereto and then, stirred at room temperature. After 4 hours, 100 mL of an ammonium chloride saturated solution is added thereto and then, extracted with dichloromethane and washed several times with water. Subsequently, an organic layer is formed from the mixture, dried with magnesium sulfate, and purified through silica column chromatography to obtain 4.2 g of Compound 8. The yield may be 40%.
$^1$H-NMR (300 MHz, CDCl3): δ 9.53 (s, 1H), 8.47 (d, 1H), 7.99 (d, 1 H), 7.46 (d, 1H), 7.18 (d, 1H), 2.61 (m, 2H), 1.65 (m, 2H), 1.26 (m, 18H), 0.88 (t, 3H).

Synthesis of Compound 9

30.0 g (167 mmol) of tellurophene is added to 500 ml of diethylether to prepare a cool solution (0° C.), n-butyllithium (n-BuLi, 2.5 M in hexane, 80 mL, 200 mmol) is added thereto, and the reaction mixture is fervently stirred at room temperature for 30 minutes. Additionally, the reaction mixture is stirred at 50° C. for 4 hours, and when cooled down to −50° C. Dimethyl formamide is slowly added thereto.
Subsequently, the reaction mixture is stirred at room temperature all night long, diluted with distilled water, and extracted with chloroform. Then, an organic layer is formed, dried with magnesium sulfate, and purified through silica column chromatography (ethyl acetate: hexane: chloroform=1:6:1.5) to obtain 20.0 g of Compound 9. The yield may be 57.7%.
$^1$H-NMR (300 MHz, CDCl3): δ 9.56 (s, 1H), 9.48 (d, 1H), 8.51 (d, 1H), 8.05 (m, 1H).

Synthesis of Compound 10

13.7 g (30.1 mmol) of tetrabromotheno[3,2-b]thiophene is added to 500 ml of tetrahydrofuran to prepare a cool solution (−78° C.), n-butyllithium (n-BuLi 2.5 M in hexane, 13.2 mL, 33.1 mmol) is added thereto, and the reaction mixture is fervently stirred for 2 hours. When cooled down to −78° C., Compound 9 is added thereto, and the reaction mixture is stirred at room temperature for 20 minutes. Subsequently, ammonium chloride is added thereto, and after evaporating a tetrahydrofuran solvent therefrom. Ethylacetate is used for an extraction. Then, an organic layer is formed, dried with magnesium sulfate, and washed several times with n-hexane to obtain 16.1 g of Compound 10. The yield may be 91.4%.
$^1$H-NMR (300 MHz, CDCl3): δ 8.80 (d, 1H), 7.69 (t, 1H), 7.47 (d, 1H), 4.74 (s, 1H), 2.26 (s, 1H).

Synthesis of Compound 11

16.1 g (27.5 mmol) of Compound 10 is added to 500 ml of dichloromethane to prepare a solution, and 14.3 g (44.7 mmol) of zinc(II) iodide ($ZnI_2$) and 12.1 g (192.6 mmol) of sodium cyanoborohydride ($NaBH_3CN$) are slowly added thereto at 0° C. Subsequently, the reaction mixture is stirred for 24 hours, and a saturated ammonium chloride solution is added thereto. Then, the resulting material is diluted with dichloromethane and washed several times with water, and an organic layer therefrom is passed through silica column and then, dried and evaporated with magnesium sulfate. The dried mixture is purified through silica column chromatography (ethyl acetate: hexane: chloroform=1:6:1.5) to obtain 8.2 g of Compound 11. The yield may be 52%.

$^1$H-NMR (300 MHz, CDCl3): δ 8.80 (d, 1H), 7.63 (m, 1H), 7.49 (d, 1H), 4.41 (s, 2H).

Synthesis of Compound 12

4.57 g (8.04 mmol) of Compound 11 is added to 500 ml of diethylether to prepare a cool solution (−78 ° C.), n-butyl-lithium (n-BuLi 2.5 M in hexane, 3.86 mL, 9.65 mmol) is added thereto, and the reaction mixture is fervently stirred for 2 hours. When cooled down to −78 ° C., Compound 8 is added thereto and then, stirred for 1 hour, and the reaction mixture is additionally added thereto at room temperature for 1 hour. Subsequently, ammonium chloride is added to the reaction mixture, and then, an extraction is performed by using ethylacetate. Then, an organic layer is formed, dried with magnesium sulfate, and washed with chloroform to obtain 2.9 g of Compound 12. The yield may be 67.8%.

$^1$H-NMR (300 MHz, CDCl3): δ 8.77 (d, 1H), 8.46 (d, 1H), 7.98 (d, 1H), 7.60 (m, 2H), 7.34 (d, 2H), 7.12 (d, 2H), 6.27 (s, 1H), 4.42 (s, 2H), 2.89 (s, 1H), 2.60 (m, 2H), 1.65 (m, 2H), 1.25 (m, 18H), 0.88 (t, 3H).

Synthesis of Compound 13

2.5 g (2.6 mmol) of Compound 12 is added to 500 ml of dichloromethane to prepare a solution, and 1.36 g (4.3 mmol) of zinc(II) iodide (ZnI$_2$) and 1.1 g (18.2 mmol) of sodium cyanoborohydride (NaBH$_3$CN) are slowly added thereto at 0° C. Subsequently, the reaction mixture is stirred for 24 hours, and a saturated ammonium chloride solution is added thereto. Then, the resulting material is diluted with dichloromethane and washed several times with water, and an organic layer therefrom is passed through silica column and then, dried and evaporated with magnesium sulfate. The dried mixture is purified through silica column chromatography (ethyl acetate: hexane: chloroform=1:6:1.5) to obtain 2.3 g of Compound 13. The yield may be 95%.

$^1$H-NMR (300 MHz, CDCl3): δ 8.78 (d, 1H), 7.72 (m, 1H), 7.62 (d, 1H), 7.56 (d, 1H), 7.48 (d, 1H), 7.31 (d, 2H), 7.10 (d, 2H), 4.41 (s, 1H), 4.39 (s, 1H), 2.60 (m, 2H), 1.65 (m, 2H), 1.25 (m, 18H), 0.88 (t, 3H).

Synthesis of Compound 14

A mixture of 0.12 g (0.13 mmol) of Compound 13 and 0.045 g (0.52 mmol) of copper(I)cyanide (CuCN) is added to 1.7 ml of N-methyl-2-pyrrolidone and irradiated at the highest temperature of 180° C. with 50 W for 1 hour by using a microwave reactor. The reaction solution is diluted with water and filtered to remove water and N-methyl-2-pyrrolidone. The resulting powder is dissolved in dichloromethane and washed several times with water. Subsequently, an organic layer is formed, dried and evaporated with magnesium sulfate to obtain 9.8 g of a brown solid compound. The dried compound is purified through silica column chromatography (ethyl acetate: hexane: chloroform=1:6:1.5) to obtain 0.02 g of Compound 14. The yield may be 19%.

$^1$H-NMR (300 MHz, CDCl3): δ 8.87 (d, 1H), 7.65 (m, 1H), 7.63 (d, 1H), 7.59 (d, 1H), 7.53 (d, 1H), 7.32 (d, 2H), 7.13 (d, 2H), 4.62 (s, 1H), 4.60 (s, 1H), 2.58 (m, 2H), 1.65 (m, 2H), 1.25 (m, 18H), 0.88 (t, 3H)

Synthesis of Compound 15

10 mg (0.012 mmol) of Compound 14 is added to 30 ml of dichloromethane to prepare a solution, and 0.036 ml (0.036 mmol) of a diisobutyl aluminum hydride solution (DIBALH, 1.0 M in tetrahydrofuran) is added thereto at 0 ° C. Subsequently, the reaction mixture is stirred for 5 minutes and then, added to a 1 N hydrochloric acid solution. The obtained resulting material is diluted with dichloromethane and washed several times with water, and an organic layer is formed, dried, and evaporated with magnesium sulfate to obtain a brown solid. The resulting solid is purified through silica column chromatography (chloroform: ethyl acetate=9:1) to obtain 5 mg of Compound 15. The yield may be 50%.

$^1$H-NMR (300 MHz, CDCl3): δ 10.21 (s, 1H), 10.19 (s, 1H), 8.80 (d, 1H), 7.62 (m, 1H), 7.56 (d, 1H), 7.52 (d, 1H), 7.49 (d, 1H), 7.30 (d, 2H), 7.12 (d, 2H), 4.82 (s, 1H), 4.80 (s, 1H), 2.57 (m, 2H), 1.65 (m, 2H), 1.25 (m, 18H), 0.87 (t, 3H).

Synthesis of Compound 16

5 mg (0.006 mmol) of Compound 15 is added to 2 ml of dry benzene to prepare a solution, and 50 mg of Amberlyst15 is added thereto under a nitrogen atmosphere. Subsequently, the obtained solution is refluxed all night long and then, cooled down to room temperature. Subsequently, the resulting floating matters are filtered to obtain 2 mg of Compound 16 in a solid state. The yield may be 30%.

Evaluation

A Gaussian 09 simulation (B3LYP/6-311+G (d,p) condition) is performed with respect to a structure of the compound according to Synthesis Example 1 to calculate reorganization energy, which is compared with reorganization energy of Compounds A and B.

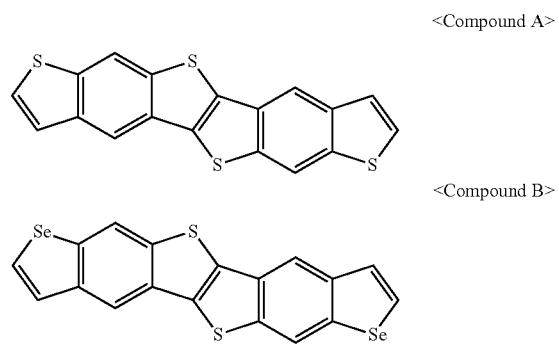

<Compound A>

<Compound B>

The results are shown in Table 1.

TABLE 1

| | Reorganization Energy (meV) |
| --- | --- |
| Compound 6 | 0.09 |
| Compound A | 0.139 |
| Compound B | 0.126 |

Referring to Table 1, the reorganization energy of the compound 6 according to Synthesis Example 1 is lower than that of Compounds A and B. Accordingly, a fused polycyclic aromatic compound having a core structure having tellurophene at the terminal end may be expected to improve electron mobility by increasing the overlap of electron orbitals compared with a fused polycyclic aromatic compound comprising only thiophene or selenophene at the terminal end.

While this disclosure has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

What is claimed is:

1. A compound represented by Chemical Formula 1A or 1B:

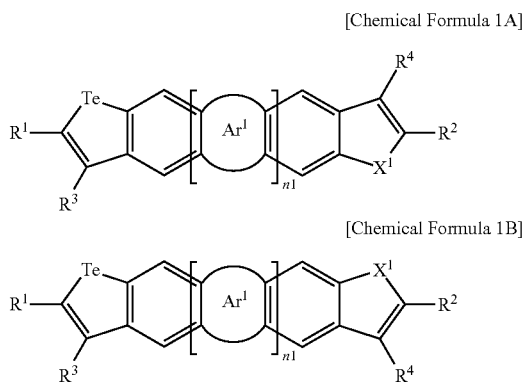

[Chemical Formula 1A]

[Chemical Formula 1B]

wherein, in Chemical Formulae 1A and 1B, $X^1$ is O, S, Se, or Te, $R^1$ to $R^4$ are each independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is 1, $Ar^1$ is one of substituted or unsubstituted rings listed in Group 1-1:

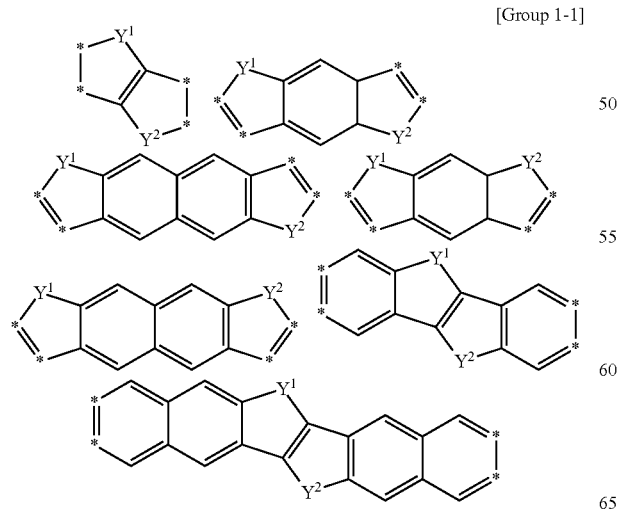

[Group 1-1]

wherein, in Group 1-1, $Y^1$ and $Y^2$ are each independently one of O, S, Se, and Te, and

* is a linking point with Chemical Formula 1A or 1B.

2. The compound of claim 1, wherein
$X^1$ is different from $Y^1$ and $Y^2$.

3. The compound of claim 2, wherein
$X^1$ is Se or Te, and
$Y^1$ and $Y^2$ are S.

4. The compound of claim 1, wherein
$R^1$ and $R^2$ are different from each other.

5. The compound of claim 4, wherein
one of $R^1$ and $R^2$ is hydrogen.

6. The compound of claim 4, wherein
one of $R^1$ and $R^2$ is a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, the other of $R^1$ and $R^2$ is a substituted or unsubstituted C3 to C30 branched alkyl group, a substituted or unsubstituted C4 to C30 branched alkenyl group, a substituted or unsubstituted C4 to C30 branched alkynyl group, or a combination thereof.

7. The compound of claim 4, wherein
one of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, the other of $R^1$ and $R^2$ is a substituted or unsubstituted C6 to C30 aryl group, a substituted or unsubstituted C6 to C30 aryloxy group, a substituted or unsubstituted C3 to C30 heteroaryl group, or a combination thereof.

8. An organic thin film comprising the compound of claim 1.

9. A thin film transistor comprising
a gate electrode,
an organic semiconductor overlapping with the gate electrode, and
a source electrode and a drain electrode electrically connected to the organic semiconductor, wherein the organic semiconductor comprises a compound represented by Chemical Formula 1A or 1B:

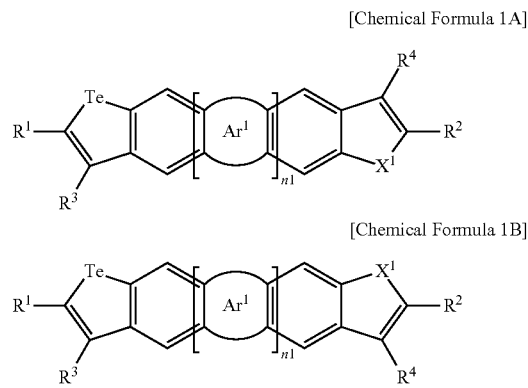

[Chemical Formula 1A]

[Chemical Formula 1B]

wherein, in Chemical Formulae 1A and 1B,
$X^1$ is O, S, Se, or Te,
$R^1$ to $R^4$ are each independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C6 to C30 aryloxy group, a substituted or unsubstituted C3 to C30 heteroaryl group, a halogen, a cyano group, or a combination thereof, and $n_1$ is 1, $Ar^1$ is one of substituted or unsubstituted rings listed in Group 1-1:

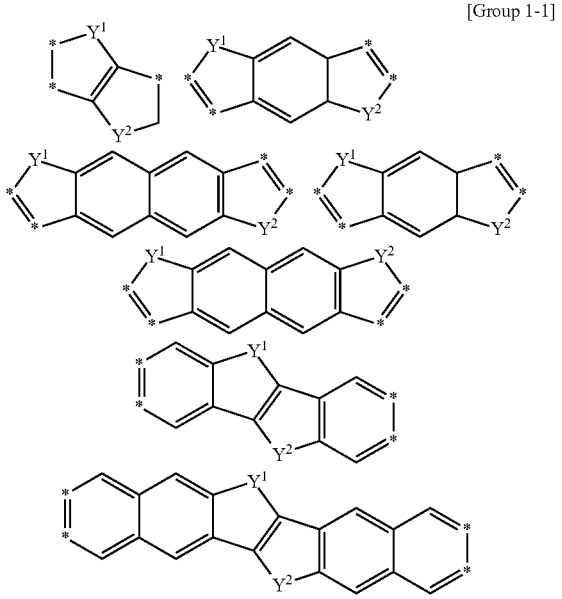

[Group 1-1]

wherein, in Group 1-1, $Y^1$ and $Y^2$ are each independently one of O, S, Se, and Te, and

* is a linking point with Chemical Formula 1A or 1B.

10. The thin film transistor of claim 9, wherein $X^1$ is different from $Y^1$ and $Y^2$.

11. The thin film transistor of claim 10, wherein $X^1$ is Se or Te, and $Y^1$ and $Y^2$ are S.

12. The thin film transistor of claim 9, wherein $R^1$ and $R^2$ are different from each other.

13. The thin film transistor of claim 12, wherein one of $R^1$ and $R^2$ is hydrogen.

14. The thin film transistor of claim 12, wherein one of $R^1$ and $R^2$ is a substituted or unsubstituted C1 to C30 linear alkyl group, a substituted or unsubstituted C2 to C30 linear alkenyl group, a substituted or unsubstituted C2 to C30 linear alkynyl group, a substituted or unsubstituted C1 to C30 alkoxy group, or a combination thereof, the other of $R^1$ and $R^2$ is a substituted or unsubstituted C1 to C30 branched alkyl group, a substituted or unsubstituted C4 to C30 branched alkenyl group, a substituted or unsubstituted C4 to C30 branched alkynyl group, or a combination thereof.

15. The thin film transistor of claim 12, wherein one of $R^1$ and $R^2$ is a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, or a combination thereof, and the other of $R^1$ and $R^2$ is a substituted or unsubstituted C6 to C30 aryl group, a substituted or unsubstituted C6 to C30 aryloxy group, a substituted or unsubstituted C3 to C30 heteroaryl group, or a combination thereof.

16. An electronic device comprising the organic thin film of claim 8.

17. An electronic device comprising the thin film transistor of claim 9.

* * * * *